United States Patent [19]

Ikeda et al.

[11] Patent Number: 4,811,740
[45] Date of Patent: Mar. 14, 1989

[54] ULTRASONIC DIAGNOSIS APPARATUS CAPABLE OF PROBE EXCHANGE

[75] Inventors: Hiroshi Ikeda; Shinichiro Umemura, both of Hachioji; Kageyoshi Katakura, Tokyo, all of Japan

[73] Assignee: Hitachi Medical Corp., Tokyo, Japan

[21] Appl. No.: 131,088

[22] Filed: Dec. 10, 1987

[30] Foreign Application Priority Data

Dec. 18, 1986 [JP] Japan ................... 61-302228

[51] Int. Cl.$^4$ ............................................. A61B 10/00
[52] U.S. Cl. ............................ 128/660.01; 128/662.03
[58] Field of Search ............... 128/660, 661, 663, 633, 128/713, 660.01, 662.03, 1 D; 73/1 R, 1 DV

[56] References Cited

U.S. PATENT DOCUMENTS

| | | | |
|---|---|---|---|
| 4,392,379 | 7/1983 | Yamaguchi | 128/660 |
| 4,399,703 | 8/1983 | Matzuk | 128/660 |
| 4,407,298 | 10/1983 | Lentz et al. | 128/713 |
| 4,446,715 | 5/1984 | Bailey | 73/1 R |
| 4,545,251 | 10/1985 | Uchida et al. | 73/1 DV |
| 4,700,708 | 10/1987 | New, Jr. et al. | 128/633 |

*Primary Examiner*—Francis Jaworski
*Attorney, Agent, or Firm*—Antonelli, Terry & Wands

[57] ABSTRACT

An ultrasonic diagnosis apparatus capable of interchangeably using a plurality of probes each having ultrasonic transducer elements disposed in an array and being detachably connected to the apparatus via a connector, wherein a storage unit is provided in the probe for storing data associated with the elements disposal configuration or control information on scanning or focusing, and a controller provided in the ultrasonic diagnosis apparatus accesses the storage unit via the connector to read the element disposal configuration data or the control information and perform a control operation of picking up an image in accordance with the read-out data.

10 Claims, 4 Drawing Sheets

ULTRASONIC DIAGNOSIS APPARATUS CAPABLE OF PROBE EXCHANGE

BACKGROUND OF THE INVENTION

The present invention relates to an ultrasonic apparatus for use in medical diagnosis or in flaw detection, and more particularly to an ultrasonic diagnosis apparatus suitable for flexibly dealing with a change in specification of a probe.

Of most of conventional ultrasonic diagnosis apparatus, an ultrasonic probe is coupled to the apparatus via a removable connector. There is known an ultrasonic apparatus of the type that it selectively uses one of a plurality of probes such as a linear array type probe having transducer elements disposed linearly, a so-called convex array type probe having transducer elements disposed circularly and the like. Among those ultrasonic apparatus, there has been proposed an ultrasonic apparatus which can discriminate a probe connected thereto among those probes. One example of such an apparatus is shown in JP-A No. 60-222766 (1985). According to this apparatus, a store means such as a shift register for storing a code representative of a probe type is mounted on a probe, and the store means is accessed by the apparatus to read the code and discriminate the type of the probe actually connected thereto.

A main memory of such a conventional ultrasonic apparatus stores scanning and focusing control data for each type of a transducer, more specifically stores data regarding the selection of transducer elements and delay amounts of transmitting and receiving signals for respective transducer elements. When a code representative of a probe type is read from a store means provided on the probe, a memory area in the main memory corresponding to the read-out code is pointed out to read therefrom control data for the connected probe. Then the probe is controlled and, imaging operation are performed by using the control data. Such a conventional ultrasonic apparatus, however, have some problems: The number of probes which can be selectively used by the apparatus is limited depending on the capacity of a main memory. In addition, if the type of probes to be used is increased or modified, it is necessary to alter the content of the main memory.

SUMMARY OF THE INVENTION

The present invention has been made in consideration of the above problems. It is an object of the present invention to eliminate the above-mentioned problems associated with conventional ultrasonic diagnosis apparatus and provide an ultrasonic diagnosis apparatus capable of flexibly dealing with a change in specification of a probe.

In an ultrasonic diagnosis apparatus which receives and transmits an ultrasonic signal by using an interchangeable array type probe to obtain an ultrasonic image of an object to be diagnosed, the above object of the present invention is achieved by providing- a store means within the probe, which store means stores at least signal control information characteristic to the probe.

According to the present invention, a memory unit is provided within a probe to store signal control information characteristic to the probe. Therefore, irrespective of probe specification, the ultrasonic diagnosis apparatus can receive the signal control information matching the specification directly from the probe, thus obviating alteration of the memory content or addition of circuits as was the case with a conventional ultrasonic diagnosis apparatus.

DESCRIPTION OF THE PREFERRED EMBODIMENTS

The embodiments of the present invention will be described in detail with reference to the accompanying drawings.

Figure 1:
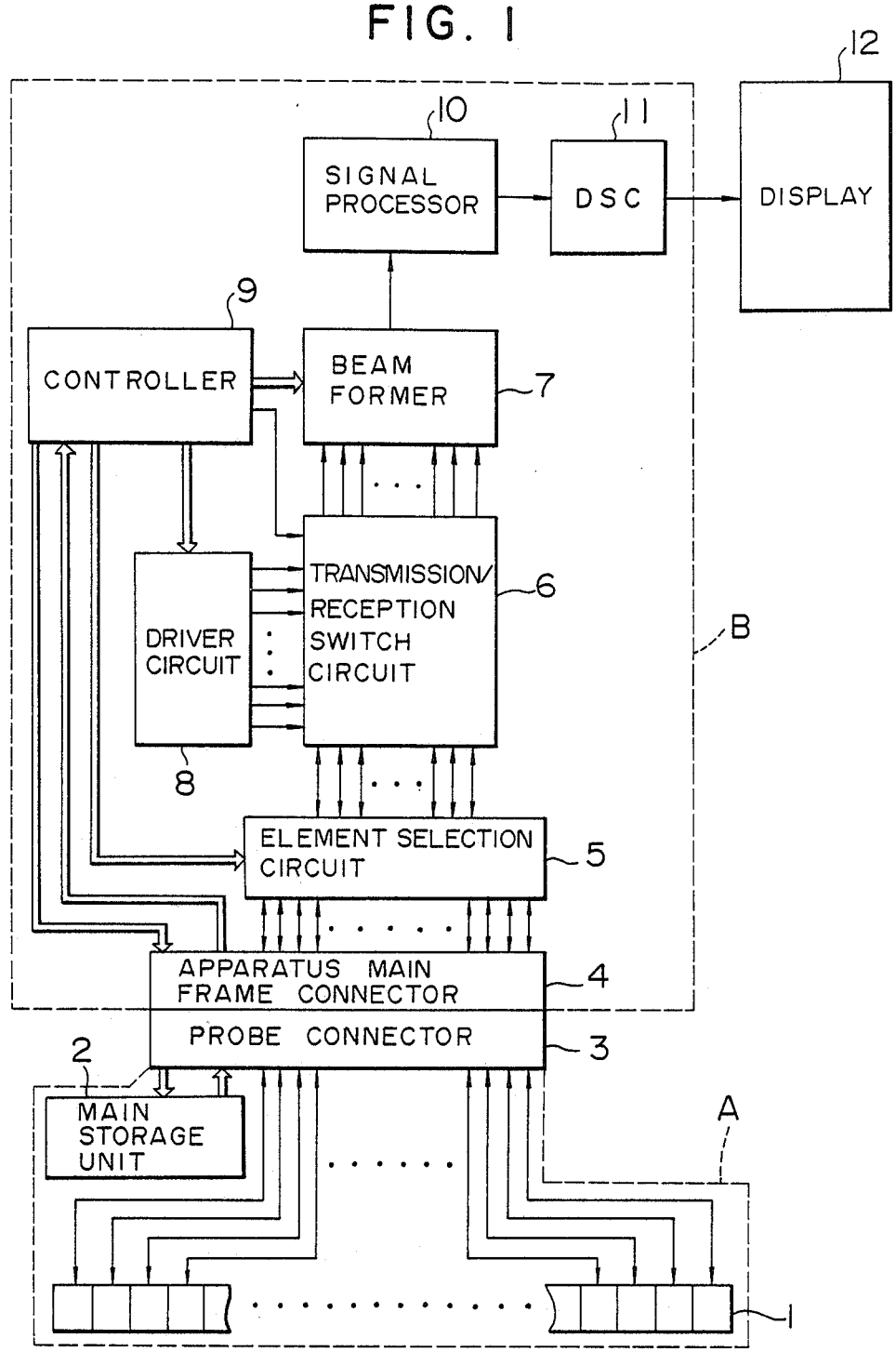
FIGS. 1 and 2 are block diagrams showing embodiments of an ultrasonic diagnosis apparatus according to the present invention.

FIG. 1 is a block diagram showing an embodiment of an ultrasonic diagnosis apparatus according to the present invention. In the Figure, a probe is indicated by reference A, and an ultrasonic diagnosis apparatus main frame is indicated by B. The probe A and the main frame B are electrically connected by an apparatus main frame connector 4 and a probe connector 3. The probe A has ultrasonic transducer elements disposed in one-dimensional array configuration. Signal lines for respective transducer elements are connected via the connectors to an element selection circuit 5 in the main frame B. A main storage unit 2 is provided in the probe A to store control data characteristic to the probe. The apparatus also comprises a transmission/reception switch circuit 6, a beam former 7, a driver circuit 8, a controller 9, a signal processor 10, a digital scan converter (DSC) 11 and a display apparatus 12.

In this embodiment, electrical scan is performed using a focused ultrasonic beam and data necessary for such scan has been stored previously in the main storage unit 2 of the probe A, the data including data for selecting transducer elements, and data for delaying transmitting and receiving signals for respective transducer elements.

In operation, first the main storage unit 2 is accessed at a predetermined address in accordance with an access signal from the controller 9, to thereby read element selection data indicating the number of a transducer element group to be used at a first transmitting and receiving operation, transmitting signal delay data indicating the delay amounts of transmitting signals for respective elements, and receiving signal delay data indicating the delay amounts of receiving signals for respective elements. The element selection circuit 5 constructed of a switch matrix selects signal lines of elements to be used in accordance with the read-out element selection data and connect them to signal lines leading to the transmission/reception switch circuit 6. The transmit signal driver circuit 8 is constructed of a plurality of presettable counters, a clock for supplying clock pulses to those counters to change the counts thereof, and a plurality of drivers for causing to generate an element driving pulse at the timing when an overflow signal is outputted from each of the counters. The read-out transmitting delay amount data is preset at the counters as their initial values. The beam former 7 is constructed of a plurality of delay lines each having intermediate taps, switches each for selecting one of the intermediate tap of an associated delay line; and an adder amplifier for adding outputs from selected intermediate taps and amplifying the added result. Which one of the intermediate taps of each delay line is selected is determined by the read-out receiving signal delay data. After the above data is preset, the controller 9 causes the transmission/reception switch circuit 6 to enter a transmit mode and activate the driver circuit 8. Thus, each counter of the driver circuit 8 starts counting clock pulses. A transmit pulse is generated each time an associated counter overflows. These generated transmit pulses are applied to selected elements via the transmission/reception switch circuit 6, the element selection circuit 5, and the connectors 4 and 3, to thereby emitting focused ultrasonic beams. Next, the controller 9 causes the transmit/receive switch circuit 6 to take a receive mode. Then, the signal lines of selected elements are caused to be connected to associated delay lines of the beam former 7. Consequently, the received signals from the selected elements, i.e., those signals generated in the selected elements by the reflected ones of the focused ultrasonic beams generated as above, are subjected to predetermined delays by associated delay lines. As a result, the beam former 7 outputs a signal which is made by matching the phases of respective received signals on a way that the phases of signals due to waves reflected from a selected focal point become to a same phase, and then, adding the signals together.

Output signals from the beam former 7 undergo various signal processing by the signal processor 10 such as detection, compression, fast time-constant control (FTC), and A/D conversion and thereafter, are inputted to the digital scan converter 11.

The above-described transmission/reception operation starting from the reading operation of the control data from the main storage unit 2 is repeated to obtain a B-mode ultrasonic image through electronic scan. Namely, the transmission/reception operation is repeated by sequentially changing the transducer elements to be selected, and data is sequentially stored in the digital scan converter 11 to form one frame of data. Signals from the digital scan converter 11 are sent to the display 12 sequentially in the order of scan lines to thereby display an ultrasonic image.

Figure 2:
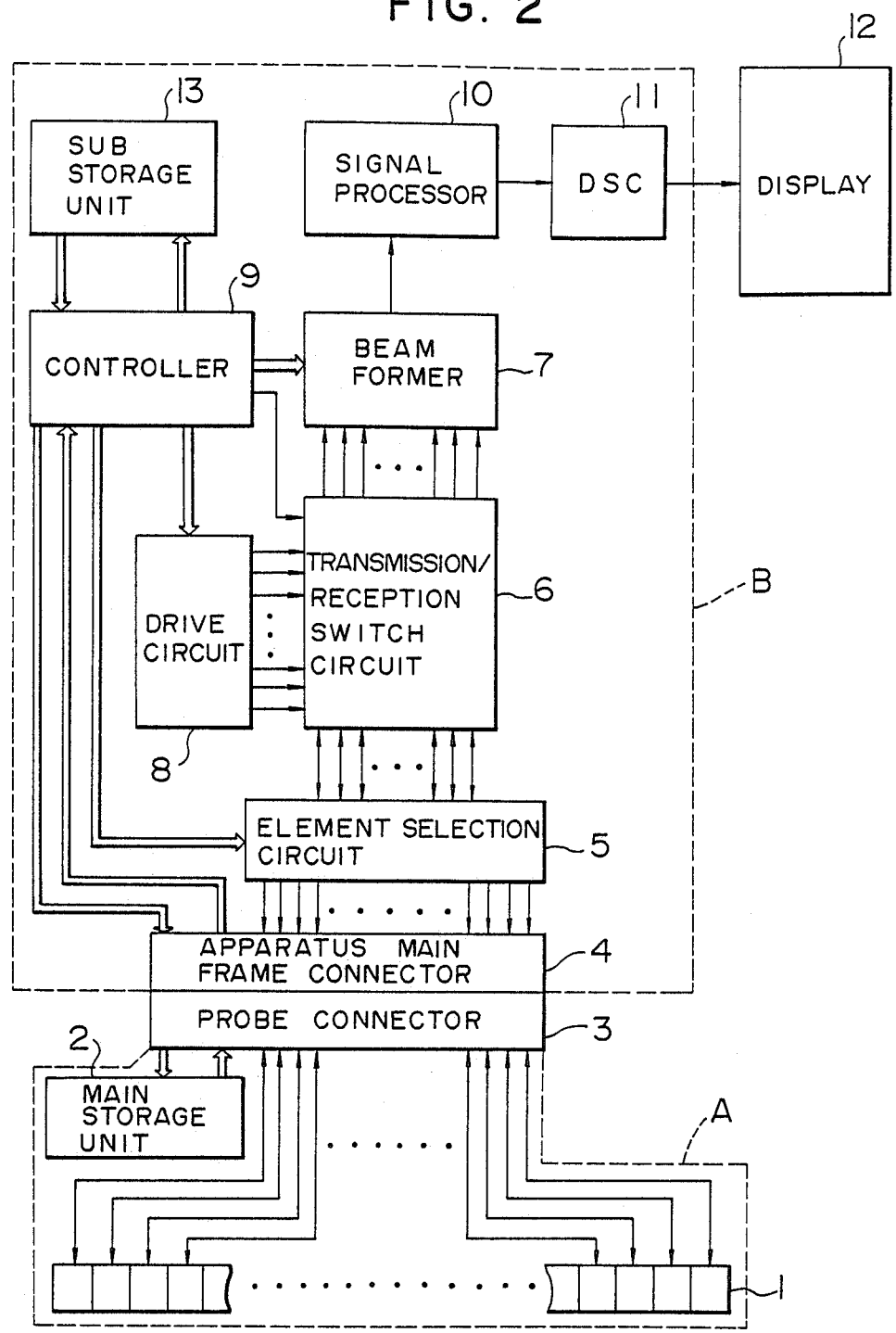

FIG. 2 is a block diagram showing another embodiment of the ultrasonic diagnosis apparatus according to the present invention. In the Figure, reference numbers 1 to 12 denote identical elements to those shown in FIG. 4. Reference number 13 denotes a sub storage unit. In this embodiment, a probe is provided with a main storage unit 2 for storing circuit control information characteristic to the probe, whereas the ultrasonic diagnosis apparatus main frame is provided with the sub storage unit 13 for temporarily storing the content of the main storage unit 2.

With a probe connected to the ultrasonic diagnosis apparatus, the content of the main storage unit 2 is read via a probe connector 3 and an apparatus main frame connector 4 under control of a controller 9. The read-out content is stored in the sub storage unit 13. Then, during a transmission/reception operation, control information stored in the sub storage unit 13 is read under control of the controller 9, thereby controlling associated circuits. Flow and process of other signals are identical to those of the first embodiment described above.

With the above circuit arrangement, signal transfer is performed only once over a relatively long signal path between the main storage unit 2 and the controller 9 so that it becomes not susceptible to the effect of noise. Further, since an access to the main storage unit 2 is performed only once when a probe is connected or the power is turned on, a storage unit having a long access time can be used as the main storage unit 2, thus resulting in low cost.

A read-only memory (ROM) and a random access memory (RAM) may be used as the main storage unit 2 and the sub storage unit 13, respectively. However, it is to be understood that the invention is not limited thereto.

Figure 3:
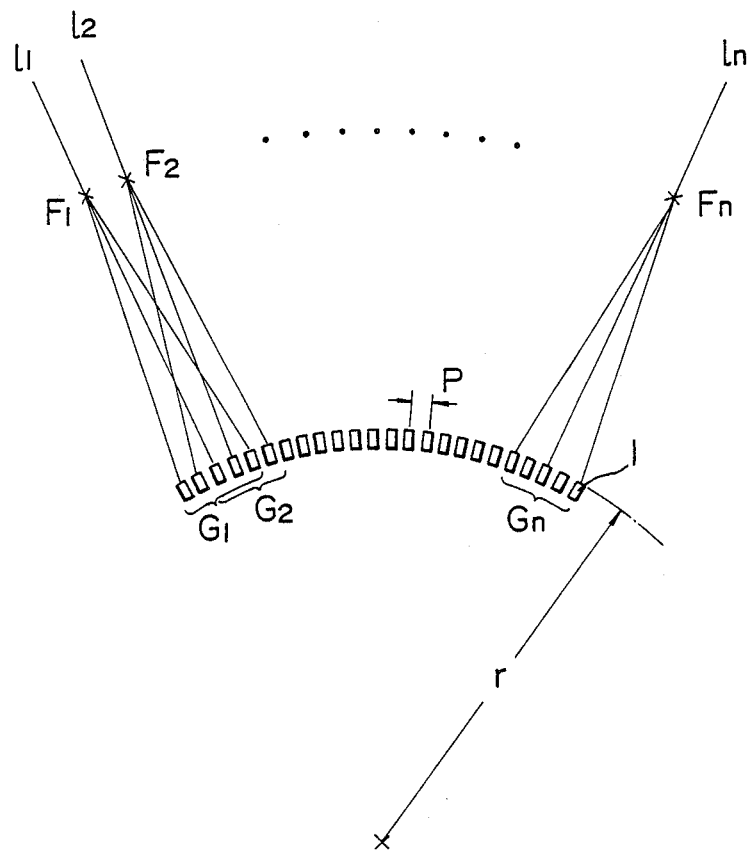
FIG. 3 is a schematic diagram showing an example of a transducer element array.

FIG. 3 shows an example of an array of transducer elements 1 of the probe A practically used in the above embodiments, the example showing a convex array type ultrasonic probe. Transducer elements are disposed at the interval of pitch P on a circular line having a radius r. Elements indicated by $G_1$ are those selected at a first transmission/reception operation, $1_1$ denotes a direction of transmitting and receiving beams at that time, and $F_1$ denotes a focus of transmitting and receiving beams. $G_2$, $1_2$ and $F_2$ denote the elements to be selected, direction and focus, respectively at a second transmission/reception operation, and $G_n$, $1_n$ and $F_n$ denote the elements to be selected, direction and focus, respectively at an nth transmission/reception operation.

Stored in the main storage units shown in FIGS. 1 and 2 are the numbers of elements to be selected sequentially for focusing and receiving ultrasonic beams onto and from the focusses $F_1, F_2, \ldots, F_n$, transmitting signal delay amount data, and receiving signal delay amount data.

If a combination of the transmitting and receiving direction and the focus location shown in FIG. 3 is applied to another probe having a different pitch P or a curvature r, it becomes necessary to select different elements and different delay amounts of transmitting and receiving signals. However, according to the above embodiments, the data representative of the element selection and the delay amounts is stored in the main storage unit 2 of a probe A so that a proper image pickup operation can be performed simply by connecting the probe via its connector 3. This is very advantageous in that a same ultrasonic diagnosis apparatus can selectively use one of a plurality of probes. It is particularly advantageous in that it is not necessary to modify the apparatus main frame B even if a probe with a different specification is used. Probes manufactured to have a same specification may have different pitches P or curvature r due to manufacture tolerance. Even in such a case, by storing control data matching each probe in the main storage unit, a correct transmission/reception of ultrasonic beams becomes possible.

Although an example of a convex array type probe is shown in FIG. 3, the invention is not limited thereto but it is also applicable to other probes such as a linear array type probe with transducer elements disposed linearly. The invention is further applicable to a probe of the type that it performs a so-called electronic sector scan control, in which, a beam is steered not by means of selective switching of transducer elements but by means of delay amount control for transmitting and receiving signals to and from transducer elements Thus, the invention is advantageous in that a same ultrasonic diagnosis apparatus can selectively use a plurality of probes including linear array type probes, convex array type probes and electronic sector scan type probes.

In the circuit arrangement of the embodiment shown in FIG. 2, not only a store function but also an arithmetic function may be implemented in the sub storage unit 13 so that the sub storage unit 13 may perform a control operation of signal processing circuits by storing information on the array pitch and curvature of a probe in the main storage unit 2. More specifically, stored in the main storage unit 2 is so-called probe structure information such as an array pitch, curvature, focus and transmitting and receiving apertures, respectively of a probe. On the other hand, stored in the sub storage unit 13 is delay time control information obtained through arithmetical operation using the above probe structure information, e.g., control information including coded values of the numbers of input/output taps of delay lines to be used, which control information is not directly associated with a probe specification.

Figure 4A:
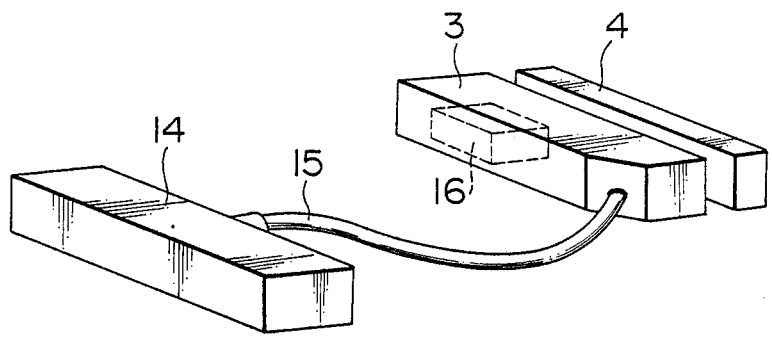
FIGS. 4A and 4B are perspective views illustrating how a memory unit is mounted on a probe.
Figure 4B:
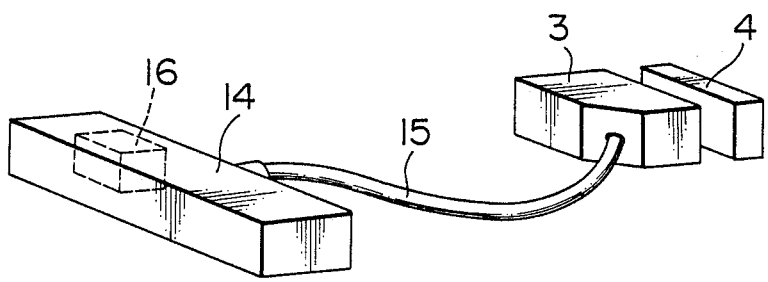

FIGS. 4A and 4B illustrate how the main storage units 2 of FIGS. 1 and 2 for storing control information characteristic to a probe are mounted on the probe. In the Figures, reference number 14 denotes a housing for a transducer array, 15 a cable, 16 the main storage unit, and 3 and 4 a probe connector and an apparatus main frame connector, respectively.

It is to be noted that the term "probe" used in the above-described embodiments is intended to cover not only the housing 14 for a transducer array but also the probe connector 3. Namely, the main storage unit 16 may be housed either in the probe connector 3 as shown in FIG. 4A or in the housing 14 for a transducer array as shown in FIG. 4B.

We claim:

1. An ultrasonic diagnosis apparatus capable of probe exchange comprising:
an image forming unit having a first connector;
a probe having a plurality of ultrasonic transducer elements disposed in a predetermined configuration;
means including a second connector associated with the probe for electrically connecting and disconnecting said probe from said image forming unit connector;
storage means physically associated with the probe for storing control information and read-out imaging procedure information unique to said probe;
said image forming unit including a control means for reading information stored in the storage means associated with said probe, said control means being connected through said connectors to control said transducer elements when transmitting signals; and
means responsive to signals received from said transducer through said connectors for forming an image using the read-out imaging procedure information.

2. An ultrasonic diagnosis apparatus capable of probe exchange according to claim 1, wherein the probe has a housing and wherein said storage means is located in said probe housing at a position adjacent said ultrasonic transducer elements.

3. An ultrasonic diagnosis apparatus capable of probe exchange according to claim 1, wherein storage means is located in said second connector.

4. An ultrasonic diagnosis apparatus capable of probe exchange according to claim 1, wherein said image forming unit has a second storage means for temporarily storing said imaging procedure information read-out from said probe storage means.

5. An ultrasonic diagnosis apparatus including an image forming unit adapted for use with a plurality of probes that can be interchangeably used wherein each of said probes has:
a plurality of ultrasonic transducer elements disposed in a predetermined configuration and connected to signal lines;
a connector for detachably and electrically connecting one of said probes to said image forming unit; and
a storage means for storing data uniquely related to the transducer element disposal configuration of said probe; and wherein the image forming unit comprises:
element selection means for selecting certain ones of said signal lines connected to said transducer elements;
transmitting means for applying a drive signal to each of said selected signal lines;
means for delaying signals received from said transducer elements via said selected signal lines and for adding together said delayed received signals in the same phase; and
control means for an imaging procedure wherein the control information in said probe is used to effect a transducer element selection sequence by said element selection means.

6. An ultrasonic diagnosis apparatus capable of probe exchange according to claim 5, wherein said control information in said probe includes also data for delay amount for signals received from said transmitting means.

7. An ultrasonic diagnosis apparatus capable of probe exchange according to claim 5, wherein said image forming unit has a second storage means for temporarily storing said imaging procedure information read-out from said probe storage means.

8. An ultrasonic diagnosis apparatus including an image forming unit adapted for use with a plurality of probes that can be interchangeably used wherein each of said probes has:
a plurality of ultrasonic transducer elements disposed in a predetermined configuration and connected to signal lines;
a connector for detachably and electrically connecting one of said probes to said image forming unit; and
a storage means for storing control information uniquely related to the transducer elements in said probe; and wherein the image forming unit comprises:
element selection means for selecting certain ones of said signal lines connected to said transducer elements;
transmitting means for applying a drive signal to each of said selected signal lines;
means for delaying signals received from said transducer elements via said selected signal lines and for adding together said delayed received signals in the same phase; and
control means for an imaging procedure wherein said means generates signals which serve as means for controlling an amount of delay for said transmitting means.

9. An ultrasonic diagnosis apparatus capable of probe exchange according to claim 8, wherein said control means generates further signals related to transducer element disposal configuration in said probe.

10. An ultrasonic diagnosis apparatus capable of probe exchange according to claim 8, wherein said image forming unit has a second storage means for temporarily storing said imaging procedure information read-out from said probe storage means.

* * * * *